United States Patent [19]
Takezawa et al.

[11] Patent Number: 5,774,228
[45] Date of Patent: Jun. 30, 1998

[54] DETERIORATION DIAGNOSIS METHOD AND DEVICE OF ELECTRICAL MACHINE AND APPARATUS

[75] Inventors: Yoshitaka Takezawa, Hitachinaka; Yuzo Ito, Mito; Shigekatsu Sato, Juou-machi, all of Japan

[73] Assignee: Hitachi, Ltd., Tokyo, Japan

[21] Appl. No.: 883,317

[22] Filed: Jun. 26, 1997

[30] Foreign Application Priority Data

Jun. 28, 1996 [JP] Japan ................................ 8-168961

[51] Int. Cl.⁶ .......................................... G01N 21/00
[52] U.S. Cl. ............................. 356/432; 356/433
[58] Field of Search ................................. 356/432, 433, 356/434, 435, 436, 445, 446, 448

[56] References Cited

U.S. PATENT DOCUMENTS 5,151,590  9/1992  Takamoto et al. ................... 356/432

FOREIGN PATENT DOCUMENTS 3-226651  10/1991  Japan .
7-272939  10/1995  Japan .

OTHER PUBLICATIONS

Polymer Engineering and Science, Feb. 1996, vol. 36, No. 4, "Nondestructive Diagnosis of Thermal Aging for Opaque Epoxy Resin by Optical Reflective Analysis", Y. Takazawa et al, pp. 587–591.

*Primary Examiner*—Hoa Q. Pham
*Attorney, Agent, or Firm*—Fay, Sharpe, Beall, Fagan, Minnich & McKee

[57] ABSTRACT

In order to diagnose non-distructively the deterioration degree of such as insulation oil and insulation paper during operation of an oil filled electrical machine and apparatus without stopping the operation thereof, a deterioration degree disgnosis method for the oil filled electrical machine and apparatus makes use of optical fibers (6, 7) and oil immersed probe (5) and diagnoses the deterioration degree of an insulation paper non-distructively based on reflection absorbance difference between those for any two wavelengths of the insulation paper.

14 Claims, 6 Drawing Sheets

5,774,228

DETERIORATION DIAGNOSIS METHOD AND DEVICE OF ELECTRICAL MACHINE AND APPARATUS

BACKGROUND OF THE INVENTION

1. Technical Field of the Invention

The present invention relates to a deterioration diagnosis method and device which permits diagnosis of deterioration degree of such as of mineral oil series insulation oil, insulation medium such as liquid per-fluorocarbon and cellulose series insulation material used for an oil filled electrical machine and apparatus, a resin material for a resin mold insulation type electrical machine and apparatus and an insulation material for a gas such as $SF_6$ gas insulation type electrical machine and apparatus without destruction thereof used in an electrical machine and apparatus during the operation thereof without stopping the operation.

2. Conventional Art

JP-A-7-272939 (1995) discloses a diagnosis method of estimating such as deterioration degree and life time of such as insulation oil and insulation paper used in an oil filled electrical machine and apparatus in which such as frufural, carbon monoxide and carbon dioxide which are decomposition products of the insulation paper are extracted from the insulation oil, gas analysis is performed thereon and deterioration degree of the insulation paper is estimated based on a correlation diagram between gas generation amount and polymerization remaining rate of the insulation paper which was determined in advance.

In the above prior method, since the amount of gas generated in association with deterioration is extremely small, a special measure for extracting the generated gas was necessitated as well as a large size evaluation device for gas analysis was required which make the above diagnosis method inconvenience.

Further, although the life time of such apparatus is controlled by the deterioration degree of the insulation paper, in the above method the deterioration degree of the insulation paper is not directly diagnosed, but the diagnosis is performed indirectly on the decomposition products of the insulation paper dissolved in the insulation oil. Therefore, if, for example, the insulation oil such as for a medium size transformer and a small size transformer is exchanged, an accurate measurement value of total decomposition products can not already been obtained which was one of problems.

SUMMARY OF THE INVENTION

An object of the present invention is to resolve the above problems and to provide a deterioration diagnosis method and device which permits diagnosis of deterioration degree of such as of mineral oil series insulation oil, insulation medium such as liquid per-fluorocarbon and cellulose series insulation material used for an oil filled electrical machine and apparatus, a resin material for a resin mold insulation type electrical machine and apparatus and an insulation material for a gas such as $SF_6$ gas insulation type electrical machine and apparatus without destruction thereof used in an electrical machine and apparatus during the operation thereof without stopping the operation.

The present inventors investigated relationships between deterioration degree of such as insulation oil and insulation paper used in oil filled electrical apparatuses and optical properties thereof and invented a diagnosis method and a diagnosis device through which the deterioration degree can be judged based on variation of transmission light intensity of the insulation oil and variation of reflection light intensity of the insulation paper due to thermal deterioration thereof. Namely, as illustrated in FIG. 4 an average polymerization remaining rate and reflection absorbance difference of the insulation paper have showed a good correlation. The principle of the present invention is as follows.

(1) A deterioration diagnosis method and device of an electrical machine and apparatus of the present invention in which irradiation light from a light source of at least two kinds of homogeneous light sources having different wavelengths each other is introduced inside the electrical machine and apparatus via an irradiation use optical fiber, emitting light from the irradiation use optical fiber is transmitted through insulation medium having transmission distance a, thereafter, enters into a light receiving use optical fiber which is guided to the outside of the electrical machine and apparatus and is transferred and introduced into a light quantity measurement unit, is characterized in that, the deterioration diagnosis method and device comprises the steps of: adjusting the intensities of the light source of homogeneous lights so that all of the intensities thereof at the light quantity measurement unit shows a constant value; thereafter introducing irradiating light from the light source of homogeneous light into the inside of the electrical machine and apparatus via the irradiation use optical fiber; irradiating a surface of an insulation material located at a position having transmission distance of a/2; guiding reflecting light from the surface of the insulation material to the light quantity measurement unit by making use of the light receiving use optical fiber which guides the reflection light from the surface of the insulation material to the outside of the electrical machine and apparatus; calculating in a deterioration degree processing unit reflection absorbances ($A\lambda$) for the respective wavelengths according to equation (1) based on the output value from the light quantity measurement unit; processing either reflection absorbance difference ($\Delta A\lambda$) between those of any two wavelengths according to equation (2) or reflection absorbance ratio ($A\lambda'$) between those of any two wavelengths according to equation (3); and further processing by comparison a relationship between deterioration degree of the insulation material to be measured which is stored in advance in a form of master curve and either the processed reflection absorbance difference or the processed reflection absorbance ratio to thereby judge the deterioration degree of the insulation material, $$A\lambda = -\log(R\lambda/100) \qquad (1)$$

$$\Delta A\lambda = A\lambda 1 - A\lambda 2 \text{ (wherein } \lambda 1 < \lambda 2) \qquad (2)$$

$$A\lambda' = A\lambda 1/A\lambda 2 \text{ (wherein } \lambda 1 < \lambda 2) \qquad (3)$$

wherein reflectance of the insulation material to be measured at wavelength $\lambda$(nm) is assumed as $R\lambda$(%).

For the light source of homogeneous light a semiconductor laser (LD) and a light emitting diode (LED) having a peak wavelength of 650~1310 nm are preferable, because they are easily available, and show a long life time and a stable performance. In particular, the LD and LED light source having a peak wavelength such as 655, 660, 670, 780, 820, 830, 850, 1300 and 1310 nm is preferable. With a light source having a wavelength other than the above range, the detection range of a detector (a light quantity measurement unit) is exceeded even when the deterioration of an object to be measured is comparatively small which may cause the light measurement impossible. When the original color of the object to be measured is pale, it is further preferable to use a light source having a peak wavelength less than 800 nm such as 655, 660, 670, 780 and 800 nm. On the other hand, when the object to be measured is originally colored, it is further preferable to use a light source having a peak wavelength near infrared range such as 780, 800, 820, 830, 850, 1300 and 1310 nm.

(2) A deterioration diagnosis method and device of an electrical machine and apparatus in which irradiation light from a halogen lamp irradioraing continuous white color light is introduced via a spectroscope inside the electrical machine and apparatus with an irradiation use optical fiber, emitting light from the irradiation use optical fiber is transmitted through insulation medium having transmission distance a, thereafter, enters into a light receiving use optical fiber which is guided to the outside of the electrical machine and apparatus and is transferred and introduced into a light quantity measurement unit, characterized in that the deterioration diagnosis method and device comprising the steps of: measuring wavelength dependency of the irradioration light intensity; thereafter introducing irradiating light from the halogen lamp into the inside of the electrical machine and apparatus via the irradiation use optical fiber; irradiating a surface of an insulation material located at a position having transmission distance of a/2; guiding reflecting light from the surface of the insulation material to the light quantity measurement unit by making use of the light receiving use optical fiber which guides the reflection light from the surface of the insulation material to the outside of the electrical machine and apparatus; calculating in a deterioration degree processing unit reflection absorbances ($A\lambda$) for the respective wavelengths according to equation (1) based on the output value from the light quantity measurement unit; processing either reflection absorbance difference ($\Delta A\lambda$) between those of any two wavelengths according to equation (2) or reflection absorbance ratio ($A\lambda'$) between those of any two wavelengths according to equation (3); and further processing by comparison a relationship between deterioration degree of the insulation material to be measured which is stored in advance in a form of master curve and either the processed reflection absorbance difference or the processed reflection absorbance ratio to thereby judge the deterioration degree of the insulation material, $A\lambda = -\log(R\lambda/100)$ (1)

$\Delta A\lambda = A\lambda 1 - A\lambda 2$ (wherein $\lambda 1 < \lambda 2$) (2)

$A\lambda' = A\lambda 1 / A\lambda 2$ (wherein $\lambda 1 < \lambda 2$) (3)

wherein reflectance of the insulation material to be measured at wavelength $\lambda$(nm) is assumed as $R\lambda(\%)$.

Variation of reflection absorbance spectrum in association with thermal deterioration of organic materials such as insulation paper and mold resin is generally represented by the curves shown in FIG. 3.

As illustrated in FIG. 3, the reflection absorbance extremely increases at the side of short wavelengths of a visible range in association with deterioration thereof, therefore, if a light source having a peak wavelength less than 650 nm is used, because of limitation of measurement range of the detector (light quantity measurement unit) it is substantially difficult to continue measurement of reflection absorbance of a material used until the life time point of the machine and apparatus concerned. The extreme increase of the reflection absorbance at the side of short wavelengths is primarily caused by the increases of electron transition absorption loss due to deterioration reaction by thermal oxidation of the material.

Further, in association with the increase of the deterioration degree, the reflection absorbance $A\lambda$ increases more at the side of short wavelengths, therefore, reflection absorbance difference $\Delta A\lambda(=A\lambda 1 - A\lambda 2)$ between those of any two wavelengths or reflection absorbance ratio $A'\lambda(=A\lambda 1/A\lambda 2)$ between those of any two wavelengths also increases, wherein $\lambda 1 < \lambda 2$. For example, when assuming the reflection absorbance difference $\Delta A\lambda$ between those of wavelength $\lambda 1$ (nm) and wavelength $\lambda 2$ (nm) as and $\alpha 1$, $\alpha 2$ and $\alpha 3$ in the order according to materials having larger deterioration degree, the relationship $\alpha 1 > \alpha 2 > \alpha 3$ stands. The same is true with respect to the reflection absorbance ratio $A\lambda'$.

These variations in such as reflection absorbance difference and reflection absorbance ratio in association with the thermal deterioration are correlated with variations of a variety of material properties of materials and through measurement of these reflection absorbance parameters the decrease of material properties of the materials can be non-destructively diagnosed. For example, a relationship between average polymerization remaining degree and reflection absorbance difference of an insulation paper in an oil filled transformer shows a good correlation as illustrated in FIG. 4.

The deterioration degree is generally represented by reduced time $\theta$ as disclosed in JP-A-3-226651(1991). When the deterioration degree is expressed by reduced time $\theta$, and if materials having variety of thermal histories show same reduced time $\theta$, their deterioration degree is implied as same. The reduced time $\theta(h)$ is defined by the following equation (4).

$$\theta = \int_t^0 \exp(-\Delta E/RT)dt \quad (4)$$

Wherein, $\Delta E$ is an apparent activation energy for thermal deterioration (J/mol), R is gas constant (J/K/mol), T is absolute temperature for thermal deterioration and t is deterioration time (h). $\Delta E$ of such as resins and oils can be easily calculated by plotting variation of reflection absorbance difference or reflection absorbance ratio for the deterioration temperature of a few kinds thereof according to Arrhenius's law.

When assuming the reduced time $\theta_0$ is at the life time point of an apparatus using an insulation oil and an insulation paper which is determined beforehand, the difference $\Delta\theta(=\theta_0-\theta)$ with reduced time $\theta$ determined based on actual measurement is a reduced time representing the remaining life time which can be used as a measure for judging the deterioration degree. Namely, the remaining life time $\Delta\theta(h)$ is expressed by the following equation (5).

$$\Delta\theta = \theta_0 - \theta = \int_t^{t0} \exp(-\Delta E/RT)dt \quad (5)$$

When the use temperature condition of the apparatus after time t is set, the remaining life time $\Delta t(=t_0-t)$ can be determined according to equation (5).

When diagnosing the deterioration degree of an insulation paper used in an oil filled electrical apparatus based on reflection absorbance difference ($\Delta A\lambda$) or reflection absorbance ratio ($A\lambda'$), there are no problems when the deterioration degree is low, however, when the insulation oil is colored depending on deterioration advancement, an accurate reflection absorbance can not be obtained due to absorbance by the colored insulation oil. FIG. 6 shows an example of master curves of light transmission loss difference of an insulation oil between wavelength of 660 nm and 850 nm and illustrates a tendency that when the deterioration advances the light transmission loss increases exponentially.

In order to correct absorption increase of the insulation oil in association with the deterioration thereof, in the present invention intensities of transmission light of respective wavelengths through distance a in the insulation oil is measured and correction of intensity between respective wavelengths is performed accordingly. When the intensity of reflection light of the insulation paper is measured at the distance of ½ of the transmission light path length, namely a/2, the absorption in the insulation oil through the back and fourth travel thereof is canceled out and an accurate reflection absorption value of the insulation paper is obtained.

DETAILED DESCRIPTION OF THE PREFERRED EMBODIMENT

Hereinbelow, the present invention is explained in details with reference to embodiments.

(Embodiment 1)

Figure 1:
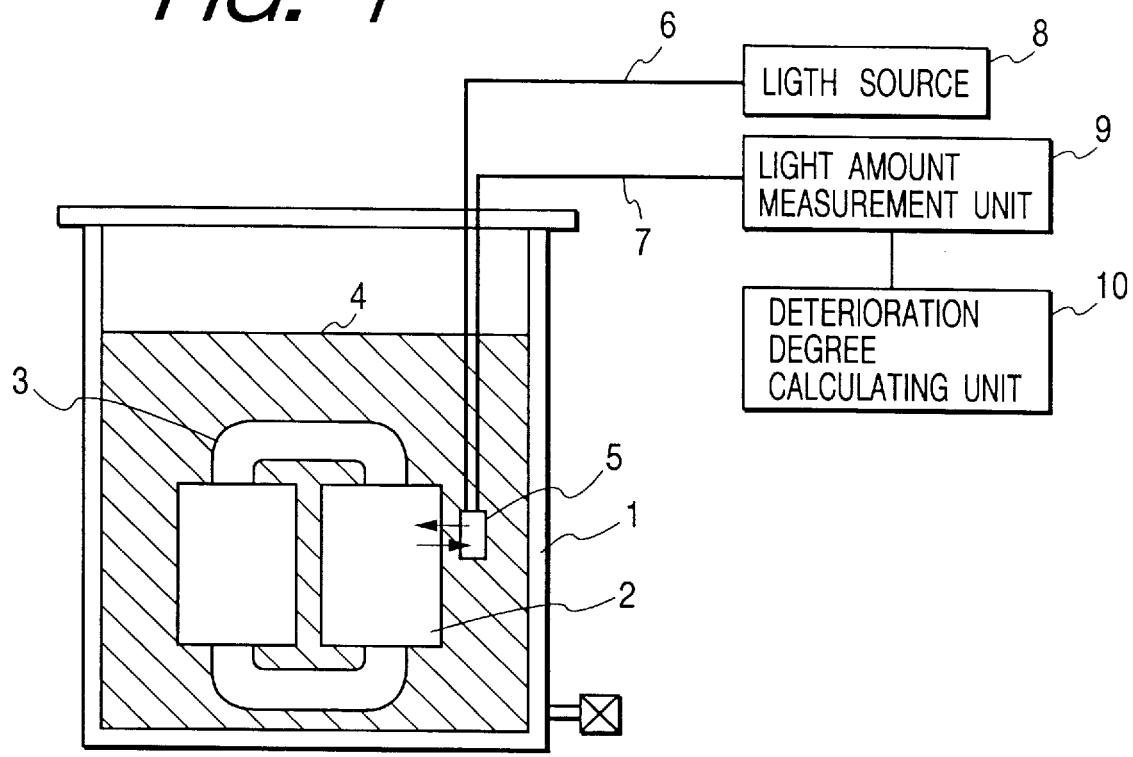
FIG. 1 is a schematic diagram showing an application manner of a deterioration diagnosis device for an oil filled electrical apparatus (transformer) according to the present invention
Figure 7:
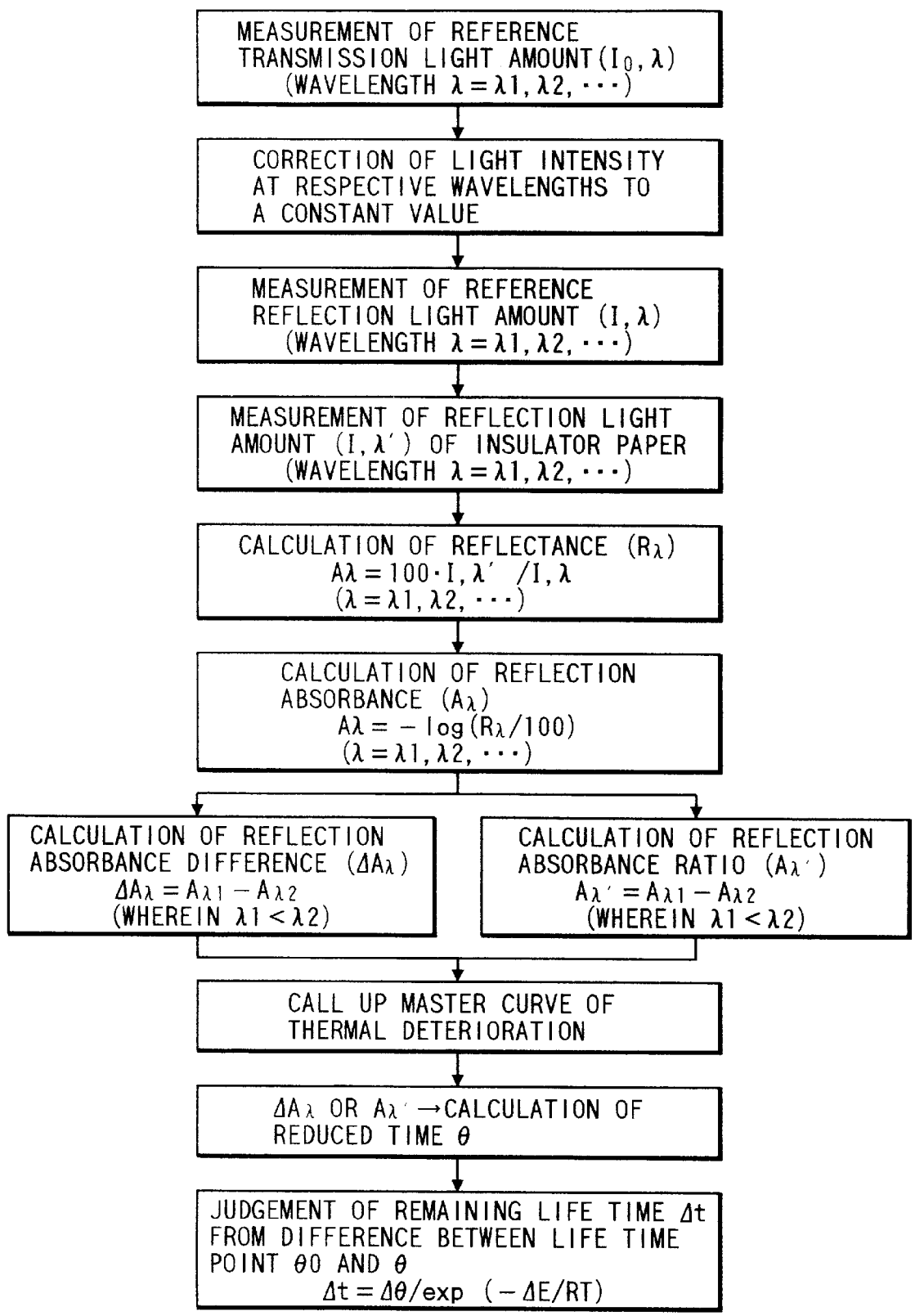
FIG. 7 is a flowchart for deterioration degree judgement processing.

FIG. 1 is a schematic diagram showing an application manner of a deterioration diagnosis device for an oil filled electrical apparatus (transformer). Further, FIG. 7 shows a flowchart of processing for judging deterioration degree.

Figure 2:
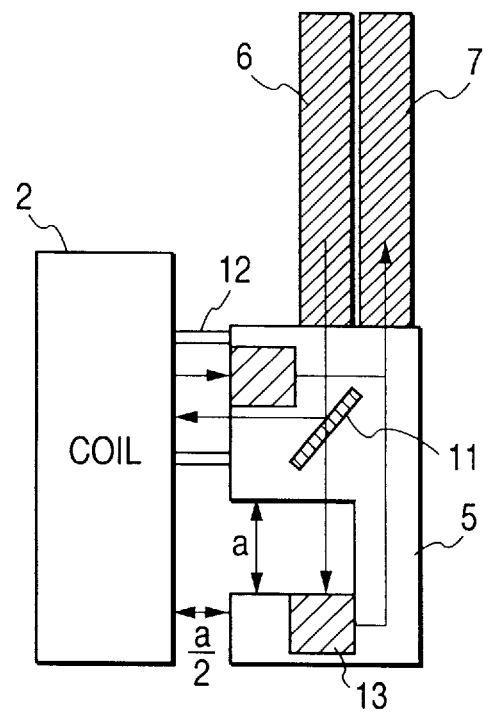
FIG. 2 is a schematic cross sectional view of a probe used in the device shown in FIG. 1.
Figure 3:
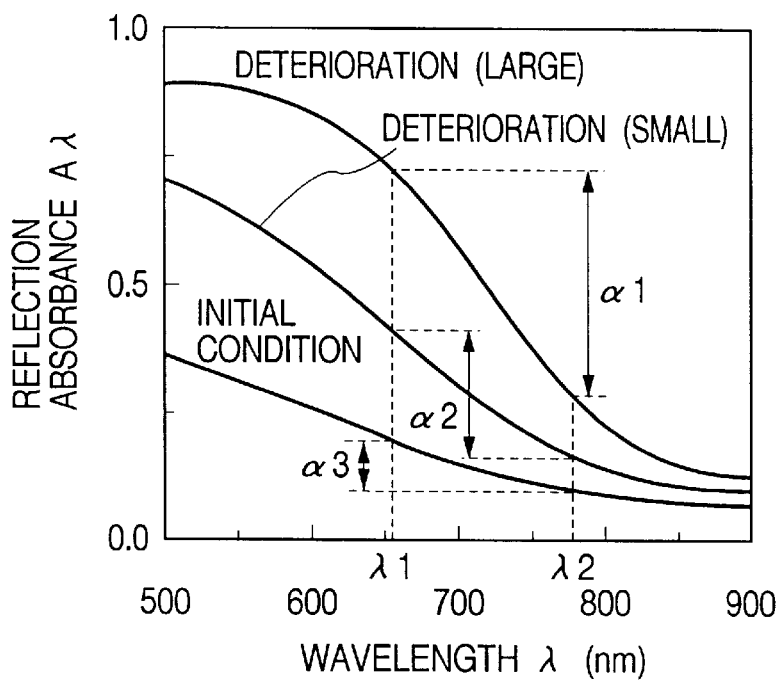
FIG. 3 is a conceptual diagram showing variation of reflection absorbance spectrum of a material.
Figure 4:
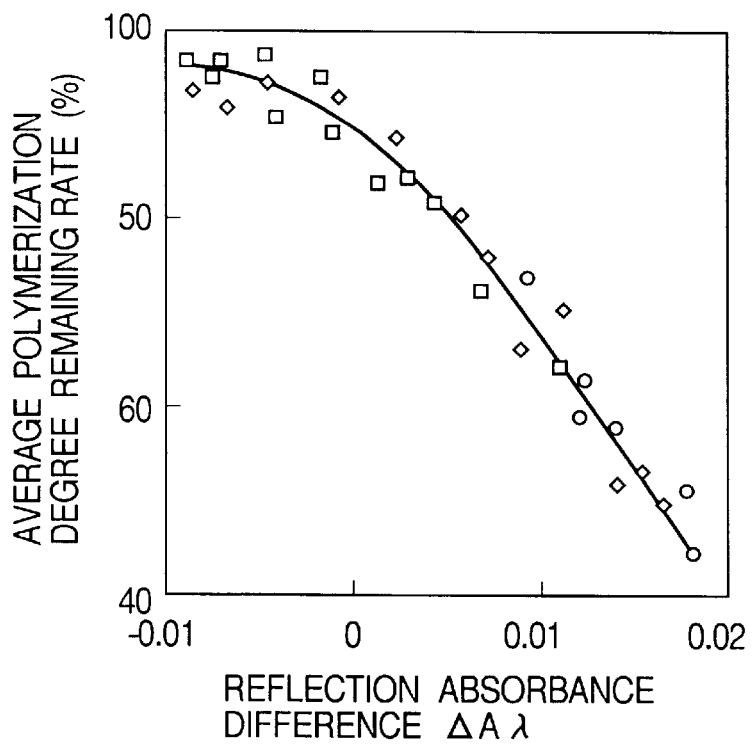
FIG. 4 is an example of diagrams showing a relationship between average polymerization remaining rate and reflection absorbance difference of an insulation paper.

In FIG. 1, a deterioration degree processing unit 10 uses a note book type personal computer having a built-in hard disk unit. At first respective transmission light quantities of respective wavelengths through an insulation oil are measured and correction is made so that the respective transmission light intensities take a constant value. In the present embodiment, a device which makes use of two wavelengths is explained. A homogeneous light having a peak wavelength $\lambda 1=660$ nm which is generated from a light source unit 8 incorporating two kinds of LED light sources is introduced to an irradiation use optical fiber 6, reaches into a probe 5 as shown in FIG. 2, passes a half mirror 11 and thereafter is transmitted through the insulation oil having distance a.

Figure 5:
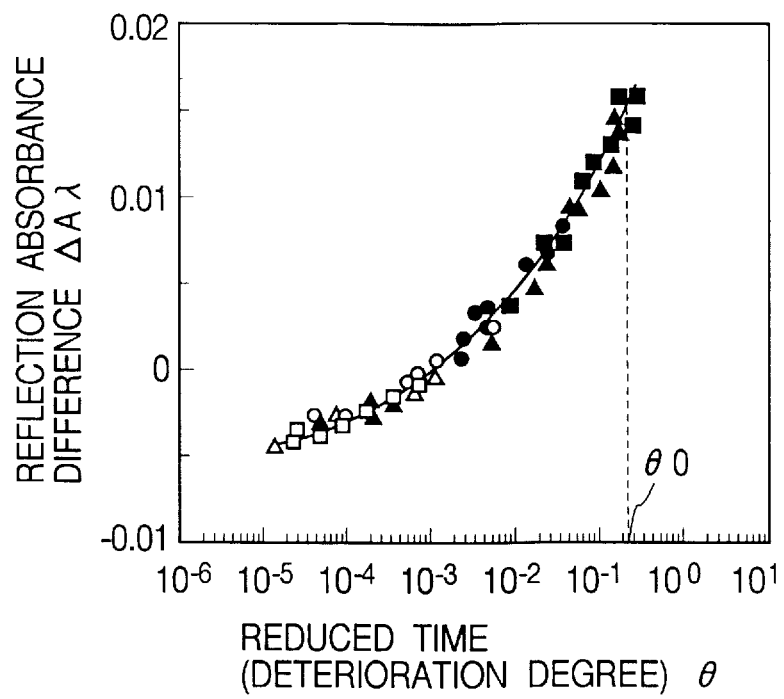
FIG. 5 is an example of reflection absorbance difference master curves serving as a reference for judging deterioration degree used in the present invention.
Figure 9:
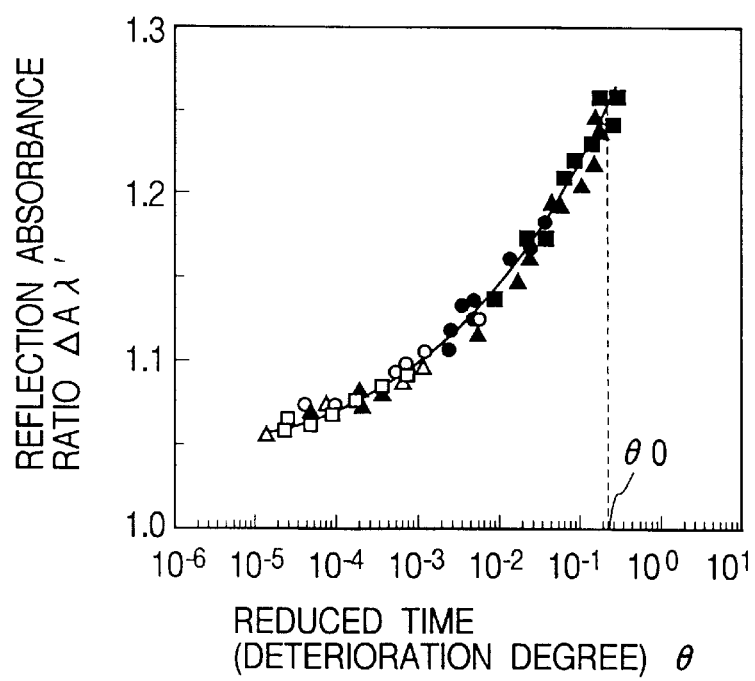
FIG. 9 is an example of reflection absorbance ratio master curves serving as a reference for judging deterioration degree in the present invention.

The transmitted light is transferred via a light receiving unit 13 and a light receiving use optical fiber 7 to a light quantity measurement unit 9. An optical power meter having a built-in photo diode is used for the light quantity measurement unit 9. The same operation is performed by making use of another homogeneous light having a peak wavelength $\lambda 2=850$ nm generated from the light source unit 8 and then a light intensity adjustment dial of the light source unit 8 is adjusted so that the transmitting light intensities for the wavelengths $\lambda 1$ and $\lambda 2$ are equated. In the present measurement the base value thereof is adjusted at 600 nW. With this operation, an influence of light absorption in association with deterioration of the insulation oil for the deterioration diagnosis of the insulation paper is corrected. Subsequently, quantity of reflection light from the insulation paper, which substantially controls the life time of an oil filled apparatus concerned, is measured. The homogeneous light having a peak wavelength $\lambda 1=660$ nm from the light source unit 8 is introduced into the irradiation use optical fiber 6 through the like operation, passes the probe 5 and is irradiated onto a surface of an insulation paper on a coil 2. A reflection light measurement unit in the probe 5 includes a shielding ring structure for interrupting stray light from the outside as illustrated in FIG. 2. Further, as shown in FIG. 2, the distance between the probe 5 and the surface of the insulation paper is designed to be ½ of the light path length used for measuring the transmission light intensity. The reflection light from the surface of the insulation paper on the coil 2 is transferred via the light receiving use optical fiber 7 to the light quantity measurement unit 9 in which reflection light quantity $I_1'$ is measured and the measurement result $I_1'$ is output to the deterioration degree processing unit 10. In the deterioration degree processing unit 10, reflectance R660(= $100 \times I_{1'/I0}$, $I_0=600$) of the homogeneous light having peak wavelength 660 nm is calculated and is stored in a memory. Like operation is performed by making use of the homogeneous light having peak wavelength $\lambda 2=850$ nm and in the deterioration degree processing unit 10, reflectance R850(= $100 \times I_2'/I_0$, $I_0=600$) of the homogeneous light having peak wavelength 850 nm is calculated and is stored in the memory. With the thus obtained reflectances of the homogeneous lights having peak wavelengths 660 and 850 nm, reflection absorbance difference $\Delta A\lambda (=A\lambda 1-A\lambda 2)$ between those of the two wavelengths or reflection absorbance ratio $A\lambda'$ $(=A\lambda 1/A\lambda 2)$ between those of the two wavelengths is determined. In the hard disk unit of the personal computer, reflection absorbance difference or reflection absorption ratio with respect to deterioration degree as shown in FIG. 5 and FIG. 9 is stored before hand in a form of master curves which are output to the deterioration degree processing unit 10 in which processing for comparison is performed on the stored function values and the reflection absorbance difference or the reflection absorbance ratio determined based on the actual measurement, and the deterioration degree is judged and then is output as the measurement result such as to an external printer (not shown).

In the present embodiment the deterioration degree measurement device of materials which makes use of two homogeneous lights having different peak wavelengths is explained, however the deterioration degree measurement device can be likely operated by making use of three homogeneous lights having different peak wavelengths and three wavelengths use master curves.

Further, the combined lights can be simultaneously irradiated in stead of the time sharing light irradiation. In this instance, it is effective if filtering is performed at the side of detector (a light quantity measurement unit). The device according to the present embodiment can be used both an on-line continuous monitering device and as a portable device performing periodic inspection of an insulation of an electric machine and apparatus.

(Embodiment 2)

Figure 8:
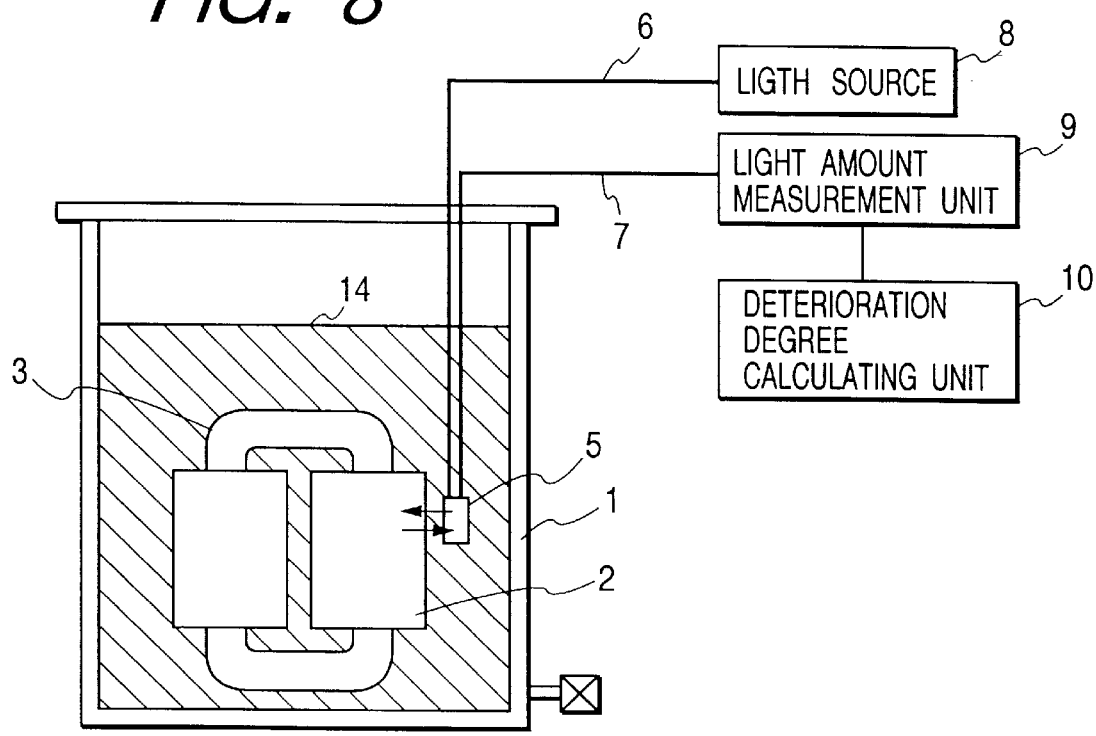
FIG. 8 is a schematic diagram showing an application manner of a deterioration diagnosis device for a liquid per-fluorocarbon filled transformer according to the present invention.

Like the embodiment 1, an embodiment 2 of a deterioration diagnosis method and device according to the present invention is applied to a transformer using liquid per-fluorocarbon 14 as insulation medium thereof as shown in FIG. 8.

At first respective transmission light quantities of respective wavelengths through the liquid per-fluorocarbon 14 are measured and correction is made so that the respective transmission light intensities take a constant value. A homogeneous light having a peak wavelength $\lambda 1=780$ nm which is generated from a light source unit 8 incorporating two kinds of LED light sources is introduced to an irradiation use optical fiber 6, reaches into a probe 5 as shown in FIG. 2, passes a half mirror 11 and thereafter is transmitted through the liquid per-fluorocarbon having distance a.

The transmitted light is transferred via a light receiving unit 13 and a light receiving use optical fiber 7 to a light quantity measurement unit 9. The same operation is performed by making use of another homogeneous light having a peak wavelength $\lambda 2=1310$ nm generated from the light source unit 8 and then a light intensity adjustment dial of the light source unit 8 is adjusted so that the transmitting light intensities for the wavelengths $\lambda 1$ and $\lambda 2$ are equated. In the present measurement the base value thereof is adjusted at 1.0 $\mu$W. Subsequently, quantity of reflection light from an insulation paper is measured. The homogeneous light having a peak wavelength $\lambda 1=780$ nm from the light source unit 8 is introduced into the irradiation use optical fiber 6 through the like operation, passes the probe 5 and is irradiated onto a surface of the insulation paper on a coil 2. The reflection light from the surface of the insulation paper on the coil 2 is transferred via the light receiving use optical fiber 7 to the light quantity measurement unit 9 in which reflection light quantity $I_1'$ is measured and the measurement result $I_1'$ is output to the deterioration degree processing unit 10. In the deterioration degree processing unit 10, reflectance $R780(=100 \times I_1'/I_0, I_0=1.0)$ of the homogeneous light having peak wavelength 780 nm is calculated and is stored in a memory. Like operation is performed by making use of the homogeneous light having peak wavelength $\lambda 2=1310$ nm and in the deterioration degree processing unit 10, reflectance R1310 $(=100 \times I_2'/I_0, I_0=1.0)$ of the homogeneous light having peak wavelength 1310 nm is calculated and is stored in the memory. With the thus obtained reflectances of the homogeneous lights having peak wavelengths 780 and 1310 nm, reflection absorbance difference $\Delta A\lambda (=A\lambda 1-A\lambda 2)$ between those of the two wavelengths or reflection absorbance ratio $A\lambda' (=A\lambda 1/A\lambda 2)$ between those of the two wavelengths is determined. In the hard disk unit of the personal computer, reflection absorbance difference or reflection absorption ratio with respect to deterioration degree as shown in FIG. 5 and FIG. 9 is stored before hand in a form of master curves which are output to the deterioration degree processing unit 10 in which processing for comparison is performed on the stored function values and the reflection absorbance difference or the reflection absorbance ratio determined based on the actual measurement, and the deterioration degree thereof is judged.

(Embodiment 3)

Figure 10:
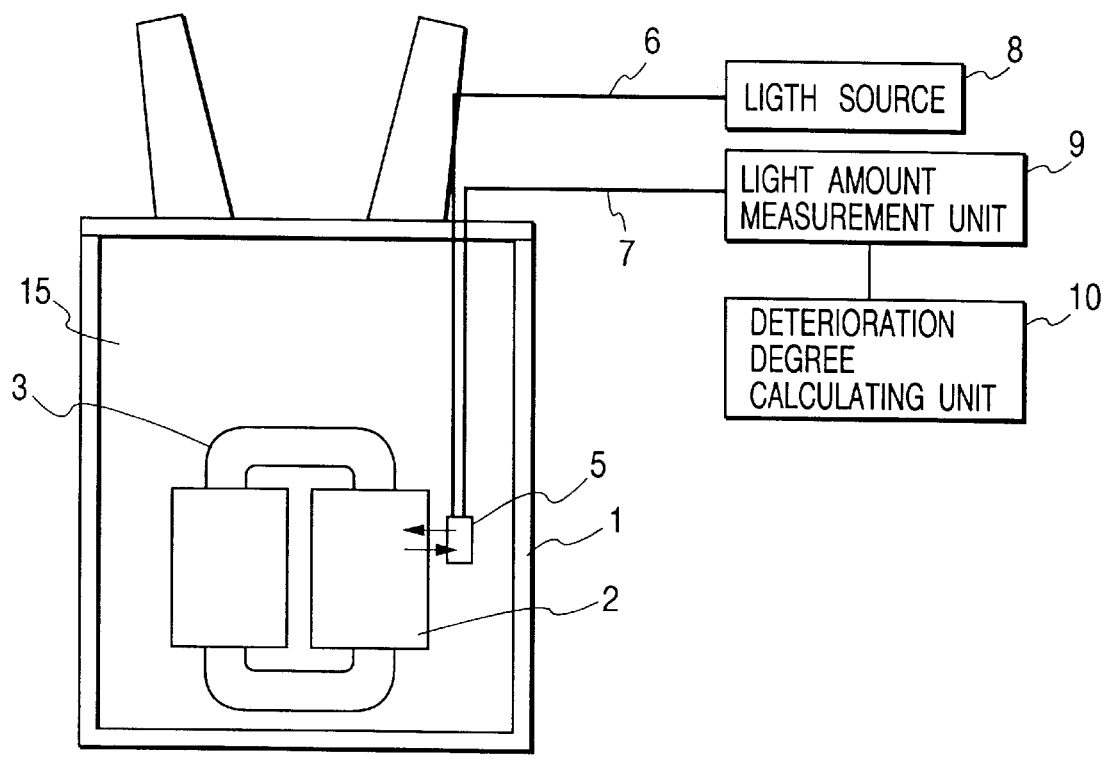
FIG. 10 is a schematic diagram showing an application manner of a deterioration diagnosis device for a $SF_6$ gas filled transformer according to the present invention.

Like the embodiments 1 and 2, an embodiment 3 of a deterioration diagnosis method and device according to the present invention is applied to a transformer using $SF_6$ gas 15 as insulation medium thereof as shown in FIG. 10.

At first respective transmission light quantities of respective wavelengths through the $SF_6$ gas are measured and correction is made so that the respective transmission light intensities take a constant value. A homogeneous light having a peak wavelength $\lambda 1=780$ nm which is generated from a light source unit 8 incorporating two kinds of LED light sources is introduced to an irradiation use optical fiber 6, reaches into a probe 5 as shown in FIG. 2, passes a half mirror 11 and thereafter is transmitted through the $SF_6$ gas having distance a.

The transmitted light is transferred via a light receiving unit 13 and a light receiving use optical fiber 7 to a light quantity measurement unit 9. The same operation is performed by making use of another homogeneous light having a peak wavelength $\lambda 2=1310$ nm generated from the light source unit 8 and then a light intensity adjustment dial of the light source unit 8 is adjusted so that the transmitting light intensities for the wavelengths $\lambda 1$ and $\lambda 2$ are equated. In the present measurement the base value thereof is adjusted at 1.5 $\mu$W. Subsequently, quantity of reflection light from an insulation paper is measured. The homogeneous light having a peak wavelength $\mu 1=780$ nm from the light source unit 8 is introduced into the irradiation use optical fiber 6 through the like operation, passes the probe 5 and is irradiated onto a surface of the insulation paper on a coil 2. The reflection light from the surface of the insulation paper on the coil 2 is transferred via the light receiving use optical fiber 7 to the light quantity measurement unit 9 in which reflection light quantity $I_1'$ is measured and the measurement result $I_1'$ is output to the deterioration degree processing unit 10. In the deterioration degree processing unit 10, reflectance $R780(=100 \times I_1'/I_0, I_0=1.5)$ of the homogeneous light having peak wavelength 780 nm is calculated and is stored in a memory. Like operation is performed by making use of the homogeneous light having peak wavelength $\lambda 2=1310$ nm and in the deterioration degree processing unit 10, reflectance R1310 $(=100 \times I_2'/I_0, I_0=1.5)$ of the homogeneous light having peak wavelength 1310 nm is calculated and is stored in the memory. With the thus obtained reflectances of the homogeneous lights having peak wavelengths 780 and 1310 nm, reflection absorbance difference $\Delta A\lambda (=A\lambda 1-A\lambda 2)$ between those of the two wavelengths or reflection absorbance ratio $A\lambda' (=A\lambda 1/A\lambda 2)$ between those of the two wavelengths is determined. In the hard disk unit of the personal computer, reflection absorbance difference or reflection absorption ratio with respect to deterioration degree as shown in FIG. 5 and FIG. 9 is stored before hand in a form of master curves which are output to the deterioration degree processing unit 10 in which processing for comparison is performed on the stored function values and the reflection absorbance difference or the reflection absorbance ratio determined based on the actual measurement, and the deterioration degree thereof is judged.

(Embodiment 4)

Figure 11:
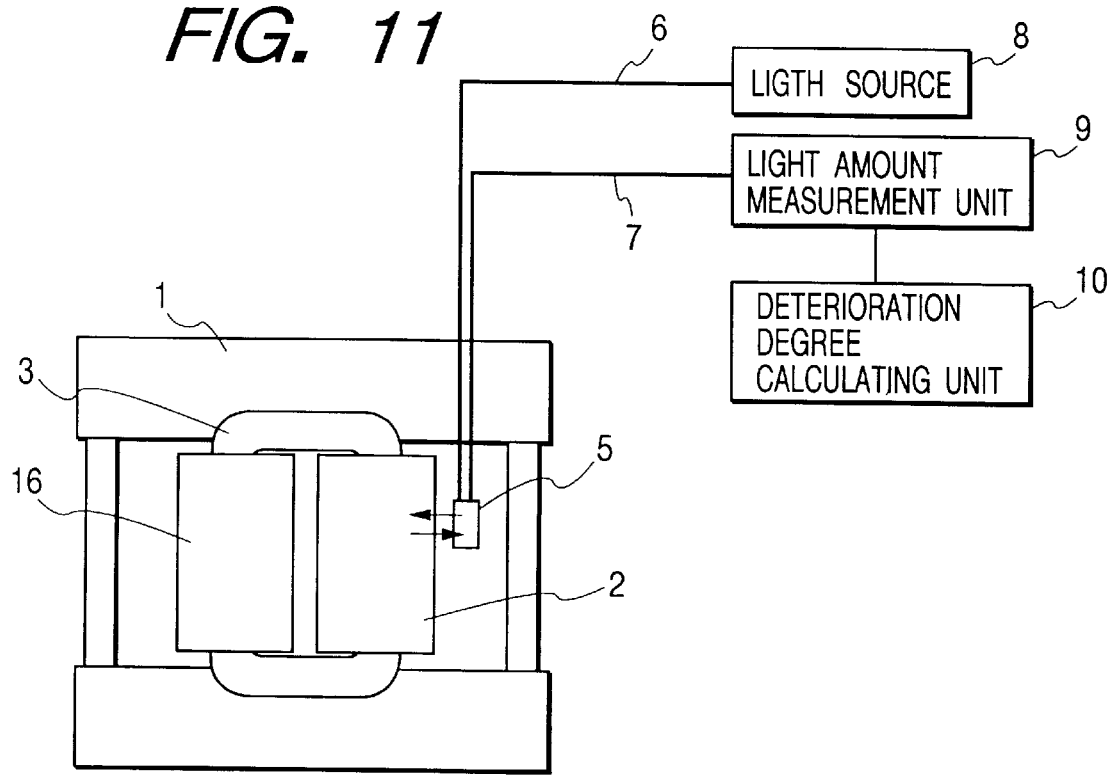
FIG. 11 is a schematic diagram showing an application manner of a deterioration diagnosis device for a resin mold dry type transformer according to the present invention.

Like the embodiments 1 through 3, an embodiment 4 of a deterioration diagnosis method and device according to the present invention is applied to a resin mold dry type transformer as shown in FIG. 11.

At first respective transmission light quantities of respective wavelengths through air serving as insulation dedium in this instance are measured and correction is made so that the respective transmission light intensities take a constant value. A homogeneous light having a peak wavelength $\lambda 1=660$ nm which is generated from a light source unit 8 incorporating two kinds of LED light sources is introduced to an irradiation use optical fiber 6, reaches into a probe 5 as shown in FIG. 2, passes a half mirror 11 and thereafter is transmitted through the air gap having distance a.

The transmitted light is transferred via a light receiving unit 13 and a light receiving use optical fiber 7 to a light quantity measurement unit 9. The same operation is performed by making use of another homogeneous light having a peak wavelength $\lambda 2=850$ nm generated from the light source unit 8 and then a light intensity adjustment dial of the light source unit 8 is adjusted so that the transmitting light intensities for the wavelengths $\lambda 1$ and $\lambda 2$ are equated. In the present measurement the base value thereof is adjusted at 800 nW. Subsequently, quantity of reflection light from the epoxy mold resin is measured. The homogeneous light having a peak wavelength $\lambda 1=660$ nm from the light source unit 8 is introduced into the irradiation use optical fiber 6 through the like operation, passes the probe 5 and is irradiated onto a surface of the epoxy mold resin on a coil 2. The reflection light from the surface of the epoxy mold resin on the coil 2 is transferred via the light receiving use optical fiber 7 to the light quantity measurement unit 9 in which reflection light quantity $I_1'$ is measured and the measurement result $I_1'$ is output to the deterioration degree processing unit 10. In the deterioration degree processing unit 10, reflectance $R660(=100 \times I_1'/I_0, I_0=800)$ of the homogeneous light having peak wavelength 660 nm is calculated and is stored in a memory. Like operation is performed by making use of the homogeneous light having peak wavelength $\lambda 2=850$ nm and in the deterioration degree processing unit 10, reflectance $R850(=100 \times I_2'/I_0, I_0=800)$ of the homogeneous light having peak wavelength 850 nm is calculated and is stored in the memory. With the thus obtained reflectances of the homogeneous lights having peak wavelengths 660 and 850 nm, reflection absorbance difference $\Delta A\lambda(=A\lambda 1-A\lambda_2)$ between those of the two wavelengths or reflection absorbance ratio $A\lambda'(=A\lambda 1/A \lambda 2)$ between those of the two wavelengths is determined. In the hard disk unit of the personal computer, reflection absorbance difference or reflection absorption ratio with respect to deterioration degree as shown in FIG. 5 and FIG. 9 is stored before hand in a form of master curves which are output to the deterioration degree processing unit 10 in which processing for comparison is performed on the stored function values and the reflection absorbance difference or the reflection absorbance ratio determined based on the actual measurement, and the deterioration degree thereof is judged.

(Embodiment 5)

Like embodiment 1, an embodiment 5 relates to a deterioration diagnosis device according to the present invention which is applied to an oil filled transformer and uses a halogen lamp irradiating continuous white color light as the light source unit 8.

At first wavelength dependency of the insulation oil is measured. The continuous light from a light source unit 8 is introduced via a spectroscope to an irradiation use optical fiber 6, reaches into a probe 5 as shown in FIG. 2, passes a half mirror 11 and thereafter is transmitted through the insulation oil having distance a.

The transmitted light is transferred via a light receiving unit 13 and a light receiving use optical fiber 7 to a light quantity measurement unit 9, wherein reference light quantities $I\lambda$ for respective wavelengths $\lambda$ is determined. Although, the measurement range of the wavelength dependency is not lmited, a range of 400~1500 nm is sufficient for the present embodiment. Subsequently, the wavelength dependency of the quantity of reflection light from an insulation paper is measured. The continuous light from the light source unit 8 is introduced into the irradiation use optical fiber 6 through the like operation, passes the probe 5 and is irradiated onto a surface of the insulation paper on a coil 2. The reflection light from the surface of the insulation paper on the coil 2 is transferred via the light receiving use optical fiber 7 to the light quantity measurement unit 9 in which reflection light quantity $I\lambda'$ is measured and the measurement result $I\lambda'$ is output to the deterioration degree processing unit 10. In the deterioration degree processing unit 10, reflectance $R\lambda(=100 \times I\lambda'/I\lambda)$ of the respective wavelengths is calculated and is stored in a memory. With the thus obtained reflectances of the respective wavelengths, reflection absorbance difference $\Delta A\lambda(=A\lambda 1-A\lambda 2)$ between those of any two wavelengths or reflection absorbance ratio $A\lambda'$ $(=A\lambda 1/A\lambda 2)$ between those of any two wavelengths is determined. In the hard disk unit of the personal computer, reflection absorbance difference or reflection absorption ratio with respect to deterioration degree as shown in FIG. 5 and FIG. 9 is stored before hand in a form of master curves which are output to the deterioration degree processing unit 10 in which processing for comparison is performed on the stored function values and the reflection absorbance difference or the reflection absorbance ratio determined based on the actual measurement, and the deterioration degree thereof is judged and then is output as the measurement result such as to an external printer (not shown).

(Embodiment 6)

Like embodiment 5, an embodiment 6 relates to a deterioration diagnosis device according to the present invention which is applied to a liquid per-fluorocarbon filled transformer and uses a halogen lamp irradiating continuous white color light as a light source unit 8.

At first wavelength dependecy of the liquid per-fluorocarbon is measured. The continuous light from the light source unit 8 is introduced via a spectroscope to an irradiation use optical fiber 6, reaches into a probe 5 as shown in FIG. 2, passes a half mirror 11 and thereafter is transmitted through the liquid per-fluorocarbon having distance a.

The transmitted light is transferred via a light receiving unit 13 and a light receiving use optical fiber 7 to a light quantity measurement unit 9, wherein reference light quantities $I\lambda$ for respective wavelengths $\lambda$ is determined. Although, the measurement range of the wavelength dependency is not limited, a range of 400~1500 nm is sufficient for the present embodiment. Subsequently, the wavelength dependency of the quantity of reflection light from an insulation paper is measured. The continuous light from the light source unit 8 is introduced into the irradiation use optical fiber 6 through the like operation, passes the probe 5 and is irradiated onto a surface of the insulation paper on a coil 2. The reflection light from the surface of the insulation paper on the coil 2 is transferred via the light receiving use optical fiber 7 to the light quantity measurement unit 9 in which reflection light quantity $I\lambda'$ is measured and the measurement result $I\lambda'$ is output to the deterioration degree processing unit 10. In the deterioration degree processing unit 10, reflectance $R\lambda(=100 \times I\lambda'/I\lambda)$ of the respective wavelengths is calculated and is stored in a memory. With the thus obtained reflectances of the respective wavelengths, reflection absorbance difference $\Delta A\lambda(=A\lambda 1-A\lambda 2)$ between those of any two wavelengths or reflection absorbance ratio $A\lambda'$ (=Aλ1/Aλ2) between those of any two wavelengths is determined. In the hard disk unit of the personal computer, reflection absorbance difference or reflection absorption ratio with respect to deterioration degree as shown in FIG. 5 and FIG. 9 is stored before hand in a form of master curves which are output to the deterioration degree processing unit 10 in which processing for comparison is performed on the stored function values and the reflection absorbance difference or the reflection absorbance ratio determined based on the actual measurement, and the deterioration degree thereof is judged.

(Embodiment 7)

Like the embodiments 5 and 6, an embodiment 7 relates a deterioration diagnosis device according to the present invention which is applied to a $SF_6$ gas insulated transformer and uses a halogen lamp irradiorating continuous white color light as a light source unit 8.

At first wavelength dependency of the $SF_6$ gas is measured. The continuous light from the light source unit 8 is introduced via a spectroscope to an irradiation use optical fiber 6, reaches into a probe 5 as shown in FIG. 2, passes a half mirror 11 and thereafter is transmitted through the $SF_6$ gas having distance a.

The transmitted light is transferred via a light receiving unit 13 and a light receiving use optical fiber 7 to a light quantity measurement unit 9, wherein reference light quantities Iλ for respective wavelengths λ is determined. Although, the measurement range of the wavelength dependency is not limited, a range of 400~1500 nm is sufficient for the present embodiment. Subsequently, the wavelength dependency of the quantity of reflection light from an insulation paper is measured. The continuous light from the light source unit 8 is introduced into the irradiation use optical fiber 6 through the like operation, passes the probe 5 and is irradiated onto a surface of the insulation paper on a coil 2. The reflection light from the surface of the insulation paper on the coil 2 is transferred via the light receiving use optical fiber 7 to the light quantity measurement unit 9 in which reflection light quantity Iλ' is measured and the measurement result Iλ' is output to the deterioration degree processing unit 10. In the deterioration degree processing unit 10, reflectance Rλ(=100×Iλ'/Iλ) of the respective light wavelengths is calculated and is stored in a memory. With the thus obtained reflectances of the respective wavelengths, reflection absorbance difference ΔAλ(=Aλ1−Aλ2) between those of any two wavelengths or reflection absorbance ratio Aλ'(=Aλ1/Aλ2) between those of any two wavelengths is determined. In the hard disk unit of the personal computer, reflection absorbance difference or reflection absorption ratio with respect to deterioration degree as shown in FIG. 5 and FIG. 9 is stored before hand in a form of master curves which are output to the deterioration degree processing unit 10 in which processing for comparison is performed on the stored function values and the reflection absorbance difference or the reflection absorbance ratio determined based on the actual measurement, and the deterioration degree thereof is judged.

(Embodiment 8)

Like the embodiments 5 through 7, an embodiment 8 relates to a deterioration diagnosis device according to the present invention which is applied to a resin mold dry type transformer and uses a halogen lamp irradiating continuous white color light as a light source unit 8.

At first wavelength depecdency of the light source is measured. The continuous light from the light source unit 8 is introduced via a spectroscope to an irradiation use optical fiber 6, reaches into a probe 5 as shown in FIG. 2, passes a half mirror 11 and thereafter is transmitted through the air gas having distance a.

The transmitted light is transferred via a light receiving unit 13 and a light receiving use optical fiber 7 to a light quantity measurement unit 9, wherein reference light quantities Iλ for respective wavelengths λ is determined. Although, the measurement range of the wavelength dependency is not limited, a range of 400~1500 nm is sufficient for the present embodiment. Subsequently, the wavelength dependency of the quantity of reflection light from an insulation paper is measured. The continuous light from the light source unit 8 is introduced into the irradiation use optical fiber 6 through the like operation, passes the probe 5 and is irradiated onto a surface of the insulation paper on a coil 2. The reflection light from the surface of the insulation paper on the coil 2 is transferred via the light receiving use optical fiber 7 to the light quantity measurement unit 9 in which reflection light quantity Iλ' is measured and the measurement result Iλ'is output to the deterioration degree processing unit 10. In the deterioration degree processing unit 10, reflectance Rλ(=100×Iλ'/Iλ) of the respective wavelengths is calculated and is stored in a memory. With the thus obtained reflectances of the homogeneous lights having peak wavelengths, reflection absorbance difference ΔAλ(=Aλ1−Aλ2) between those of any two wavelengths or reflection absorbance ratio Aλ'(=Aλ1/Aλ2) between those of any two wavelengths is determined. In the hard disk unit of the personal computer, reflection absorbance difference or reflection absorption ratio with respect to deterioration degree as shown in FIG. 5 and FIG. 9 is stored before hand in a form of master curves which are output to the deterioration degree processing unit 10 in which processing for comparison is performed on the stored function values and the reflection absorbance difference or the reflection absorbance ratio determined based on the actual measurement, and the deterioration degree thereof is judged.

(Embodiment 9)

Figure 6:
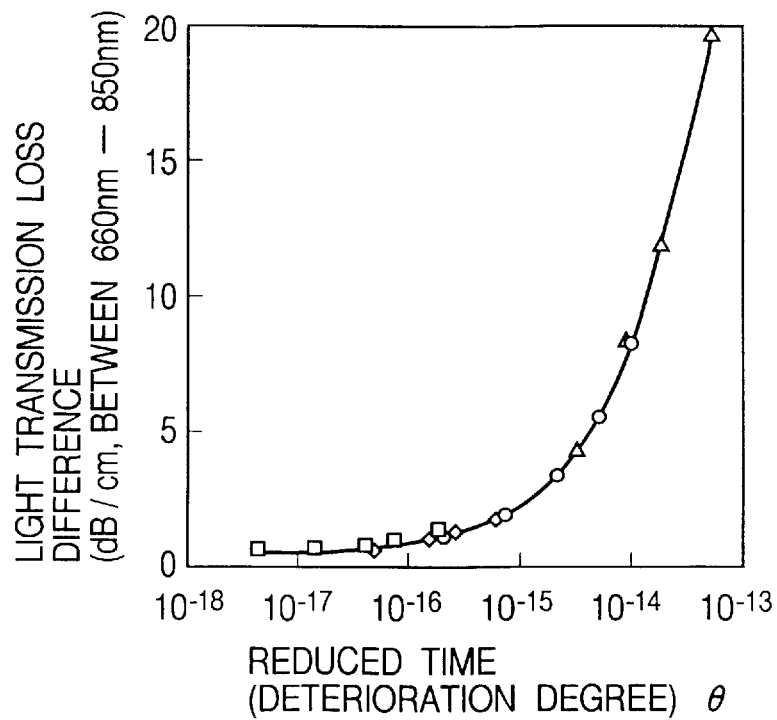
FIG. 6 is an example of light transmission loss difference master curves of an insulation oil.

An embodiment 9 relates to a deterioration diagnosis method and device according to the present invention which makes use of light transmission loss difference between those for two wavelengths through an insulation oil as a parameter with the structure of the embodiment 1. At first quantities of transmission lights through air for respective wavelengths from the light source are respectively measured. Two kinds of LED light sources (λ1=660 nm, λ2=850 nm) are used as the light source unit 8. Reference light quantities Iλ1 and Iλ2 for the respective wavelengths, when the lights have transmitted through an air gap having distance a (cm) are respectively measured. Subsequently, quantities of transmission lights through the insulation oil are likely measured. Namely, quantity of transmission light Iλ' for the homogeneous light having peak wavelength of 660 nm through the insulation oil is measured and the measurement result Iλ1' is output to the deterioration degree processing unit 10, in which light transmission loss αλ1(=−10/a×log(Iλ1'/Iλ1), wherein unit is dB/cm) for the wavelength 660 nm is calculated and the calculation result is stored in a memory. Likely, the same operation is performed by making use of the homogeneous light having peak wavelength of 850 nm and in the deterioration degree processing unit 10 light transmission loss αλ2(=−10/a×log(Iλ2'/Iλ2), wherein unit is dB/cm) for the wavelength 850 nm is calculated and the calculation result is stored in the memory. With thus obtained light transmission losses for the wavelengths 660 and 850 nm, light transmission loss difference Δαλ(=αλ1−αλ2) is determined in the deterioration degree processing unit 10. In the hard disk unit of the personal computer light transmission loss difference with respect to deterioration degree is stored in advance in a form of master curves as illustrated in FIG. 6, which is output to the deterioration degree processing unit 10 in which processing for comparison is performed on the stored function values and the light transmission loss difference of the insulation oil determined based on the actual measurement, and the deterioration degree thereof is judged.

(Embodiment 10)

An embodiment 10 relates to a deterioration diagnosis method and device according to the present invention which makes use of light transmission loss difference between those for two wavelengths through an insulation oil as a parameter with the structure of the embodiment 5. At first quantities of transmission lights through air for the continuous white color light are respectively measured. A halogen lamp is used as the light source unit 8. Reference light quantities $I\lambda$ for the respective wavelengths, when the lights have transmitted through an air gap having distance a (cm), are respectively measured. Although, the range of wavelengths $\lambda$ is not particularly limited a wavelength range of 400~1500 nm is sufficient for the present embodiment. Subsequently, quantities of transmission lights through the insulation oil are likely measured. Namely, quantity of transmission light $I\lambda'$ for the wavelength $\lambda$ through the insulation oil is measured and the measurement result $I\lambda'$ is output to the deterioration degree processing unit 10, in which light transmission loss $\alpha\lambda(=-10/a \times \log(I\lambda'/I\lambda)$, wherein unit is dB/cm) for a wavelength is calculated and the calculation result is stored in a memory. In the like manner light transmission losses for respective wavelength are obtained. With thus obtained light transmission losses for the respective wavelengths, light transmission loss difference $\Delta\alpha\lambda(=\alpha\lambda1-\alpha\lambda2)$ between those of any two wavelengths is determined in the deterioration degree processing unit 10. In the hard disk unit of the personal computer light transmission loss difference with respect to deterioration degree is stored in advance in a form of master curves as illustrated in FIG. 6, which is output to the deterioration degree processing unit 10 in which processing for comparison is performed on the stored function values and the light transmission loss difference of the insulation oil determined based on the actual measurement, and the deterioration degree thereof is judged.

According to the present invention, a deterioration diagnosis method and device can be obtained which permits diagnosis of deterioration degree of such as mineral oil series insulation oil, insulation medium such as liquid perfluorocarbon and celllose series insulation material used for an oil filled electrical machine and apparatus, a resin material for a resin mold insulation type electrical machine and apparatus and an insulation material for a gas such as $SF_6$ gas insulation type electrical machine and apparatus without destruction thereof used in an electrical machine and apparatus during the operation thereof without stopping the operation.

We claim:

1. A deterioration diagnosis method of an electrical machine and apparatus in which irradiation light from a light source of at least two kinds of homogeneous light sources having different wavelengths each other is introduced inside the electrical machine and apparatus via an irradiation use optical fiber, emitting light from the irradiation use optical fiber is transmitted through insulation medium having transmission distance a, thereafter, enters into a light receiving use optical fiber which is guided to the outside of the electrical machine and apparatus and is transferred and introduced into a light quantity measurement unit, characterized in that the deterioration diagnosis method comprising the steps of:

adjusting the intensities of the light source of homogeneous lights so that all of the intensities thereof at the light quantity measurement unit show a constant value;

thereafter introducing irradiating light from the light source of homogeneous light into the inside of the electrical machine and apparatus via the irradiation use optical fiber;

irradiating a surface of an insulation material located at a position having transmission distance of a/2;

guiding reflecting light from the surface of the insulation material to the light quantity measurement unit by making use of the light receiving use optical fiber which guides the reflection light from the surface of the insulation material to the outside of the electrical machine and apparatus;

calculating in a deterioration degree processing unit reflection absorbances ($A\lambda$) for the respective wavelengths according to equation (1) based on the output value from the light quantity measurement unit;

processing either reflection absorbance difference ($\Delta A\lambda$) between those for any two wavelengths according to equation (2) or reflection absorbance ratio ($A\lambda'$) between those for any two wavelengths according to equation (3); and further processing by comparison a relationship between deterioration degree of the insulation material to be measured which is stored in advance in a form of master curve and either the processed reflection absorbance difference or the processed reflection absorbance ratio to thereby judge the deterioration degree of the insulation material, $$A\lambda = -\log(R\lambda/100) \quad (1)$$

$$\Delta A\lambda = A\lambda1 - A\lambda2 \text{ (wherein } \lambda1 < \lambda2) \quad (2)$$

$$A\lambda' = A\lambda1/A\lambda2 \text{ (wherein } \lambda1 < \lambda2) \quad (3)$$

wherein reflectance of the insulation material to be measured at wavelength $\lambda$(nm) is assumed as $R\lambda$(%).

2. A deterioration diagnosis method of an electrical machine and apparatus according to claim 1, characterized in that either a semiconductor laser or a light emitting diode having a peak wavelength more than 650 nm and less than 1310 nm is used as the light source of homogeneous light.

3. A deterioration diagnosis method of an electrical machine and apparatus according to claim 1, characterized in that the insulation medium is one of liquid perfluorocarbon, mineral oil series insulation oil, $SF_6$ gas and air.

4. A deterioration diagnosis method of an electrical machine and apparatus according to claim 1, characterized in that the insulation material of which reflection light intensity is measured is one of cellulose series insulation paper, kraft paper, press board and mold resin.

5. A deterioration diagnosis method of an electrical machine and apparatus in which irradiation light from a halogen lamp irradiating continuous white color light is introduced via a spectroscope inside the electrical machine and apparatus with an irradiation use optical fiber, emitting light from the irradiation use optical fiber is transmitted through insulation medium having transmission distance a, thereafter, enters into a light receiving use optical fiber which is guided to the outside of the electrical machine and apparatus and is transferred and introduced into a light quantity measurement unit, characterized in that the deterioration diagnosis method comprising the steps of:

measuring wavelength dependency of the irradiation light intensity;

thereafter introducing irradiating light from the halogen lamp into the inside of the electrical machine and apparatus via the irradiation use optical fiber;

irradiating a surface of an insulation material located at a position having transmission distance of a/2;

guiding reflecting light from the surface of the insulation material to the light quantity measurement unit by making use of the light receiving use optical fiber which guides the reflection light from the surface of the insulation material to the outside of the electrical machine and apparatus;

calculating in a deterioration degree processing unit reflection absorbances ($A\lambda$) for the respective wavelengths according to equation (1) based on the output value from the light quantity measurement unit;

processing either reflection absorbance difference ($\Delta A\lambda$) between those for any two wavelengths according to equation (2) or reflection absorbance ratio ($A\lambda'$) between those for any two wavelengths according to equation (3); and further processing by comparison a relationship between deterioration degree of the insulation material to be measured which is stored in advance in a form of master curve and either the processed reflection absorbance difference or the processed reflection absorbance ratio to thereby judge the deterioration degree of the insulation material, $$A\lambda = -\log(R\lambda/100) \quad (1)$$
$$\Delta A\lambda = A\lambda 1 - A\lambda 2 \text{ (wherein } \lambda 1 < \lambda 2) \quad (2)$$
$$A\lambda' = A\lambda 1 / A\lambda 2 \text{ (wherein } \lambda 1 < \lambda 2) \quad (3)$$

wherein reflectance of the insulation material to be measured at wavelength $\lambda$(nm) is assumed as $R\lambda$(%).

6. A deterioration diagnosis method of an electrical machine and apparatus according to claim 5, characterized in that the insulation medium is one of liquid perfluorocarbon, mineral oil series insulation oil, $SF_6$ gas and air.

7. A deterioration diagnosis method of an electrical machine and apparatus according to claim 5, characterized in that the insulation material of which reflection light intensity is measured is one of cellulose series insulation paper, kraft paper, press board and mold resin.

8. A deterioration diagnosis device for an electrical machine and apparatus, characterized in that the deterioration diagnosis device comprises:

a light source including at least two kinds of homogeneous light sources having different wavelengths;

an irradiation use optical fiber which introduces irradiation light from said light source inside the electrical machine and apparatus;

a light receiving use optical fiber which, after the introduced irradiation light via said irradiation use optical fiber is transmitted through insulation medium having transmission distance a, guides the transmitted light to the outside of the electrical machine and apparatus;

a light quantity measurement unit which measures the intensity of the transmitted light guided by said light receiving use optical fiber; and a deterioration degree processing unit in which, after adjusting the intensities of the light source of homogeneous light so that all of the intensities thereof at said light quantity measurement unit shows a constant value, introducing irradiating light from said light source of homogeneous light into the inside of the electrical machine and apparatus via said irradiation use optical fiber; irradiating a surface of an insulation material located at a position having transmission distance of a/2, and guiding reflecting light from the surface of the insulation material to said light quantity measurement unit by making use of said light receiving use optical fiber which guides the reflection light from the surface of the insulation material to the outside of the electrical machine and apparatus, reflection absorbances ($A\lambda$) for the respective wavelengths are calculated according to equation (1) based on the output value from said light quantity measurement unit, either reflection absorbance defference ($\Delta A\lambda$) between those of any two wavelengths according to equation (2) or reflection absorbance ratio ($A\lambda'$) between those of any two wavelengths according to equation (3) is processed; and relationship between deterioration degree of the insulation material to be measured which is stored in advance in a form of master curve and either the processed reflection absorbance difference or the processed reflection absorbance ratio is processed by comparison to thereby judge the deterioration degree of the insulation material, $$A\lambda = -\log(R\lambda/100) \quad (1)$$
$$\Delta A\lambda = A\lambda 1 - A\lambda 2 \text{ (wherein } \lambda 1 < \lambda 2) \quad (2)$$
$$A\lambda' = A\lambda 1 / A\lambda 2 \text{ (wherein } \lambda 1 < \lambda 2) \quad (3)$$

wherein reflectance of the insulation material to be measured at wavelength $\lambda$(nm) is assumed as $R\lambda$(%).

9. A deterioration diagnosis device for an electrical machine and apparatus according to claim 8, characterized in that either a semiconductor laser or a light emitting diode having a peak wavelength more than 650 nm and less than 1310 nm is used as said light source of homogeneous light.

10. A deterioration diagnosis device for an electrical machine and apparatus according to claim 8, characterized in that the insulation medium is one of liquid perfluorocarbon, mineral oil series insulation oil, $SF_6$ gas and air.

11. A deterioration diagnosis device for an electrical machine and apparatus according to claim 8, characterized in that the insulation material of which reflection light intensity is measured is one of cellulose series insulation paper, kraft paper, press board and mold resin.

12. A deterioration diagnosis device for an electrical machine and apparatus, characterized in: that the deterioration diagnosis device comprises a light source including a halogen lamp irradiating continuous white color light;

an irradiation use optical fiber which introduces via a spectroscope irradiation light from said light source inside the electrical machine and apparatus;

a light receiving use optical fiber which, after the introduced irradiation light via said irradiation use optical fiber is transmitted through insulation medium having transmission distance a, guides the transmitted light to the outside of the electrical machine and apparatus;

a light quantity measurement unit which measures the intensity of the transmitted light guided by said light receiving use optical fiber; and a deterioration degree processing unit in which, after measuring wavelength dependency of the irradiation light intencity; introducing irradiating light from said light source of halogen lamp into the inside of the electrical machine and apparatus via said irradiation use optical fiber; irradiating a surface of an insulation material located at a position having transmission distance of a/2, and guiding reflecting light from the surface of the insulation material to said light quantity measurement unit by making use of said light receiving use optical fiber which guides the reflection light from the surface of the insulation material to the outside of the electrical machine and apparatus, reflection absorbances ($A\lambda$) for the respective wavelengths are calculated according to equation (1) based on the output value from said light quantity measurement unit, either reflection absorbance defference ($\Delta A\lambda$) between those of any two wavelengths according to equation (2) or reflection absorbance ratio ($A\lambda'$) between those of any two wavelengths according to equation (3) is processed; and relationship between deterioration degree of the insulation material to be measured which is stored in advance in a form of master curve and either the processed reflection absorbance difference or the processed reflection absorbance ratio is processed by comparison to thereby judge the deterioration degree of the insulation material, $$A\lambda = -\log(R\lambda/100) \tag{1}$$

$$\Delta A\lambda = A\lambda 1 - A\lambda 2 \text{ (wherein } \lambda 1 < \lambda 2\text{)} \tag{2}$$

$$A\lambda' = A\lambda 1 / A\lambda 2 \text{ (wherein } \lambda 1 < \lambda 2\text{)} \tag{3}$$

wherein reflectance of the insulation material to be measured at wavelength $\lambda$(nm) is assumed as $R\lambda$(%).

13. A deterioration diagnosis device for an electrical machine and apparatus according to claim 12, characterized in that the insulation medium is one of liquid perfluorocarbon, mineral oil series insulation oil, $SF_6$ gas and air.

14. A deterioration diagnosis device for an electrical machine and apparatus according to claim 12, characterized in that the insulation material of which reflection light intensity is measured is one of cellulose series insulation paper, kraft paper, press board and mold resin.

* * * * *